US008473277B2

(12) United States Patent
Jephcott

(10) Patent No.: US 8,473,277 B2
(45) Date of Patent: Jun. 25, 2013

(54) TRANSLATION STATION

(76) Inventor: David Lynton Jephcott, Shropshire (GB)

(*) Notice: Subject to any disclaimer, the term of this patent is extended or adjusted under 35 U.S.C. 154(b) by 214 days.

(21) Appl. No.: 12/850,787

(22) Filed: Aug. 5, 2010

(65) Prior Publication Data

US 2012/0035906 A1 Feb. 9, 2012

(51) Int. Cl.
*G06F 17/28* (2006.01)
(52) U.S. Cl.
USPC ............... 704/3; 704/277; 382/115; 715/264; 715/706
(58) Field of Classification Search
USPC ... 704/8, 270, 277, 3; 715/706, 264; 382/115, 382/116
See application file for complete search history.

(56) References Cited

U.S. PATENT DOCUMENTS

| | | | | |
|---|---|---|---|---|
| 4,507,750 A * | 3/1985 | Frantz et al. | ...................... | 704/3 |
| 4,805,132 A * | 2/1989 | Okamoto et al. | .................. | 704/3 |
| 4,882,681 A * | 11/1989 | Brotz | ................. | 704/3 |
| 4,984,177 A * | 1/1991 | Rondel et al. | ................. | 704/277 |
| 5,384,701 A * | 1/1995 | Stentiford et al. | ............. | 704/277 |
| 6,061,646 A * | 5/2000 | Martino et al. | ................... | 704/3 |
| 6,073,146 A * | 6/2000 | Chen | ............. | 715/264 |
| 6,192,332 B1 * | 2/2001 | Golding | ............. | 704/2 |
| 6,434,518 B1 * | 8/2002 | Glenn | ............. | 704/3 |
| 6,925,438 B2 * | 8/2005 | Mohamed et al. | ............. | 704/276 |
| 7,643,985 B2 * | 1/2010 | Horvitz | ............. | 704/2 |
| 8,275,602 B2 * | 9/2012 | Curry et al. | ............. | 704/3 |
| 2005/0192811 A1 * | 9/2005 | Parks et al. | .................. | 704/277 |
| 2007/0100637 A1 * | 5/2007 | McCune | ............. | 704/277 |
| 2007/0213988 A1 * | 9/2007 | Hanson | ............. | 704/275 |
| 2008/0086759 A1 * | 4/2008 | Colson | ............. | 726/2 |
| 2008/0262827 A1 * | 10/2008 | DeGroot | ............. | 704/3 |
| 2009/0089066 A1 * | 4/2009 | Gao et al. | ............. | 704/277 |
| 2009/0132234 A1 * | 5/2009 | Weikel | ............. | 704/3 |
| 2010/0083148 A1 * | 4/2010 | Finn et al. | ............. | 715/764 |

* cited by examiner

*Primary Examiner* — Martin Lerner
(74) *Attorney, Agent, or Firm* — Thomas W. Tolpin; Tolpin & Partners, PC

(57) ABSTRACT

An interactive electronic translation and communications process is provided for use in a translation station that provides a mobile or stationary fixed interactive facility for interviews or interrogations to be carried out between two persons speaking in different languages. The process can be assisted by animated virtual characters (avatars) realistically created and displayed on a computer screen to represent ethnic looks from around the globe. The avatars can be lip synchronized to deliver messages to the interviewee in the interviewee's languages and can guide the users and interviewee through a series of questions and answers. Biometric conditions of the interviewee and electronic identification of the interviewee can also be readily accomplished by the novel process. The process is particularly useful for hospitals, law enforcement, military, airport security, transportation terminals, financial institutions, and government agencies.

20 Claims, 7 Drawing Sheets

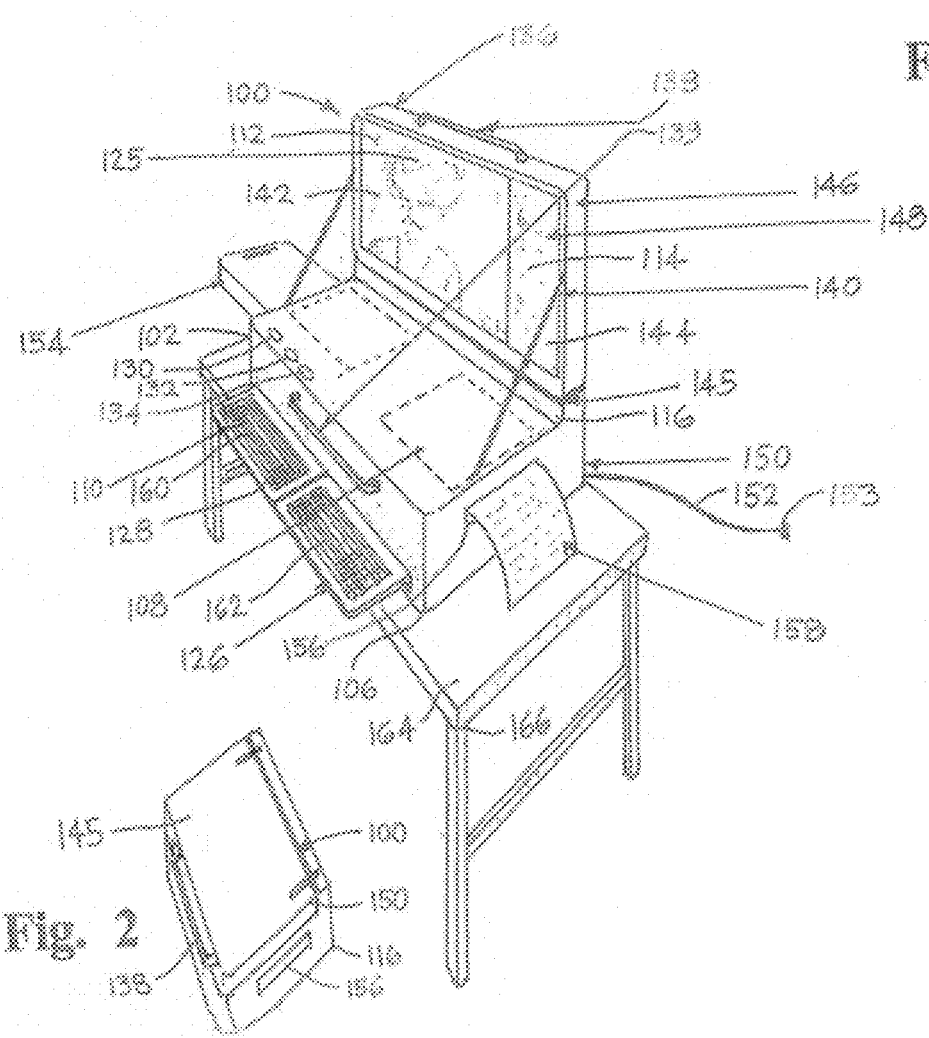

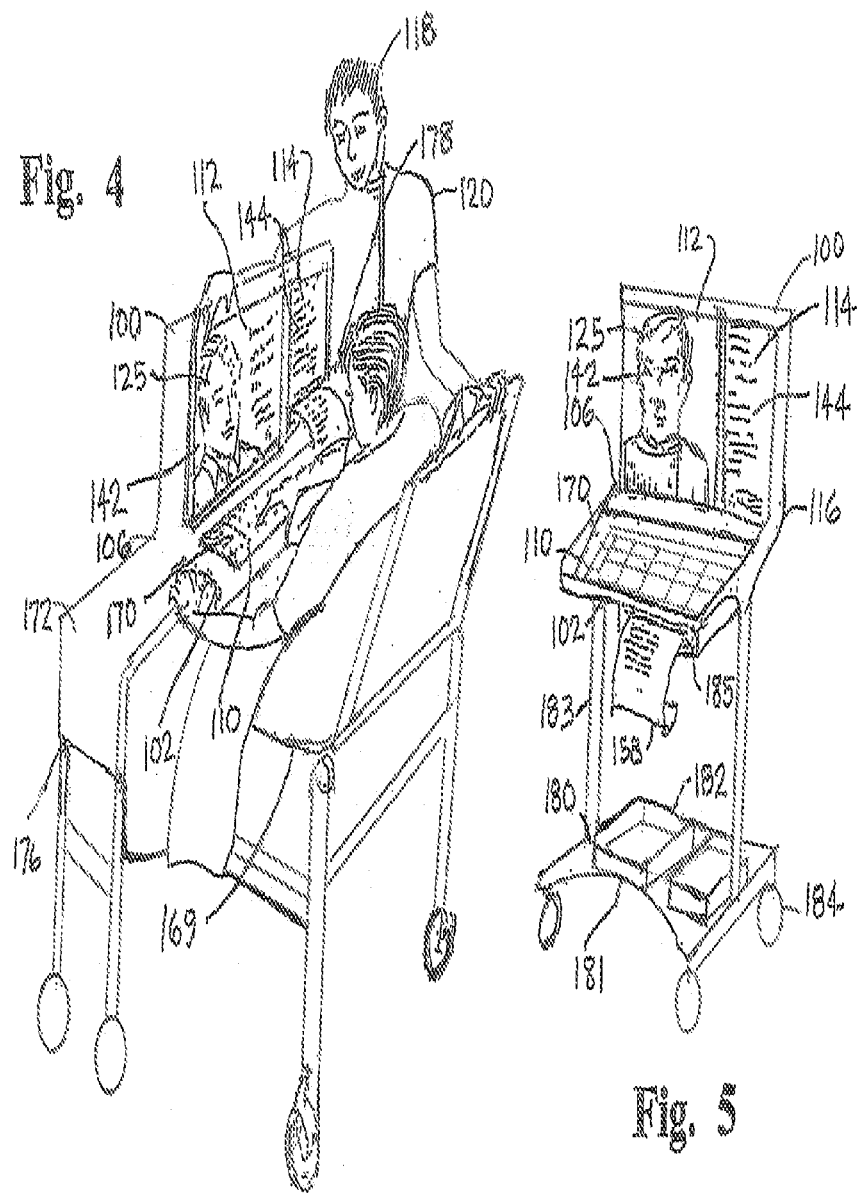

TRANSLATION STATION

BACKGROUND OF THE INVENTION

This invention relates to electronic translation equipment, and more particularly, to an interactive electronic translation and communications process for translating language to and from an individual.

Often in medical situations, law and order enforcement, and border control zones, it is necessary to obtain the services of human translators in order to converse or question individuals who speak a different language. Such translators may not be readily available which can cause undue delays, frustration and expenses. Moreover, in medical emergencies such delays can be life threatening.

Assuming a human translator can be located for a person who speaks a different language, an interview can be conducted between three people: (1) the interviewer, such as a doctor, nurse, or a policeman; (2) the interviewee, such the patient, suspect or other person; and (3) the translator. During a sequence of questions and answers, the interviewer can inform the interviewee of their situation or dilemma and will request an understanding or confirmation of these facts from the interviewee. If the interviewee responds in the affirmative, then the translators' job has been done. A record of the interview and written authorization from the patient will help allow a medical procedure to be carried out.

Prior interrogation systems are flawed in that many suspects brought to trial often state that their confession was illegally obtained because it was not understood properly and that the translator did not ask certain questions during the interview. The lawyer for the accused suspect is often successful to prevent the admission of or confession on the grounds that his client does not understand the translator or the translated questions. Such situations are unproductive and a burden to courts.

In medical cases, wherein a patient does not speak the native language or is injured in such a manner as to preclude speech, it means that the doctors or surgeons have to make life threatening decisions as to the procedures that need to be undertaken. If a medical procedure proceeds without patient consent and results in impairment or even death, then as a consequence litigation is likely to follow. If the doctors decide not to proceed without proper consent from the patient or a representative and the patient suffers as a result of the delay or even dies, then once again the doctors face charges of malpractice, neglect and probable litigation. Litigation costs the medical world enormous amounts of money and could be avoided or minimized by a better process or procedure. Therefore, translation is vital in hospitals where patients are at risk and a decision needs to be taken urgently to save life or to carry out a medical procedure of crucial importance to the patient well-being. Therefore, where a patient is incapable of speech or does not speak the language, it is required that a translator be present if possible, at a cost to the health service provider or the insurance company involved. Locating a translator may take too long with potentially dire consequences. Hospitals and senior medical staff are always placed in a difficult situation in such situations.

Human behavioral patterns have been studied and analyzed by scientists. Behavioral patterns can be detected in handwriting, body language, temperature changes and various human mannerisms.

There has been a major upsurge in people movement around the world and migrant and immigrant populations are putting a huge strain on government resources everywhere. These resources are needed to monitor and manage border controls ensuring safety for citizens and to protect inhabitants from acts of terrorism. Also, because of the upsurge in people entering or immigrating to numerous countries, there has been a sharp rise in costs associated with translation services that are needed to communicate with these peoples in many languages and dialects.

Reliance on human translators is costly and burdensome for immigration officers, police forces, the judiciary, medical facilities, welfare agencies, and other government offices. The need and availability of reliable translators also creates many logistical problems.

In law enforcement, the police typically have to deal with many situations on the road in cities, towns and in other remote locations away from their headquarters. The need to obtain witness statements and or to communicate with a suspect or victim often requires a translator. A witness, victim or suspect may speak a different language. Police or other law enforcement personnel are obliged to obtain statements and information and often have to arrange for local translators to be on site where victims, witnesses or suspects do not speak the native language.

In military operations and applications, there is a great need to be able to communicate with indigenous populations involved in conflicts around the world and it is vital for interrogation as well as rebuilding the infrastructure of the societies. The use of translators is a highly dangerous occupation and human translators are often targeted and killed while carrying out their duties.

It is, therefore, desirable to provide an improved communications process, which overcomes most, if not all of the preceding problems.

BRIEF SUMMARY OF THE INVENTION

An improved interactive electronic translation and communications process is provided which is effective, efficient and economical. Advantageously, the novel interactive electronic translation and communications process is easy to use, readily transportable and convenient. Desirably, the user friendly interactive electronic translation and communications process is reliable, durable and helpful. Among the many other advantages of the novel interactive electronic translation and communications process are: no waiting for translators to arrive; audit trails carried out locally, and links to online databases for verification of identity and information given.

The interactive electronic translation and communications process can include a combination of computer software linked with animated avatars that are programmed to translate conversations online and offline in many, if not all of the languages and dialects of the world. The avatars can be modeled on humans from many, if not all, of the races and ethnicities of the world. The avatars can be realistic with lip synchronized speech. The avatars can also be featured in various settings as applicable to the culture or nationality that are created around them. The background settings can be external and/or internal. The avatars can be linked to touch screen keypads that allow the user(s) to input information as selected by the interviewee or as directed by an interviewer, such as officials in border control, law enforcement, doctors, physicians, nurses, dentist, hospital staff, medical technician, dental technician, administrative assistant, policeman, detective, interrogator, soldier, military personnel, bank official, security personnel, airport official, transportation personnel, government official, immigration officer; teacher, school official, university or college administrator, or representative of a company, or other individuals.

Menu driven question and answer scenarios can be used that offer translations of information quickly in any language for use in hospitals, border crossings or other passport control zones, security areas, as well as for military use, law and order enforcement, and other uses.

A mobile kiosk or other translation station can be useful in hospitals of other places. The kiosk or other translation station can support a screen, monitor or other display showing avatars of different races. An electronic selection tool, buttons or images can be displayed on the screen, such as the globe or flags of countries of the world, so that the interviewer can ask the patient or other interviewee to select their nationality should it not be known. If the information cannot be easily relayed, then the computer system can record the voice of the patient or other interviewee and produce some suggestions as to the nationality via voice and/or language recognition. This can be done by picking up on key words that the software will recognize, such as German, Russian, Chinese, Spanish, French, Korean, Japanese, Afghanistan, Arabic, etc. The computer system can also have dialect and speech recognition software to detect and understand the dialect and speech of the patient or other interviewee.

Once the language has been identified then the doctor, law enforcement officer, border control guard, immigration official, or other interviewer, can commence a menu driven question and answer program. These questions can be carefully crafted in key areas of information gathered and will invite the patient, suspect or other interviewee to respond yes and no. These responses can be logged and saved as a record as part of an audit trail. At the end of the interview, the patient, suspect of other interviewee can be asked to agree that their responses are accurate and complete at which time the kiosk or other translation station will produce a printed document with the same reference identity code and the recipient can be asked to sign it twice once alongside the declaration in his own language and secondly in a paragraph written in the host language. The declaration or other document can be signed and witnessed by another person. The preceding provides an audit trail that has been signed and witnessed thereby protecting doctors, police, border control officers, and other official interviewers as well as establishing evidence of the interviewee's response.

The computer system preferably can have or access software comprising a computer program that can translate communications into many languages and can be linked via an avatar displayed on a computer screen and linked to a printer. The computer system can record a conversation in writing or orally. The computer system can also produce a printed, visual and/or audio audit trail document, which memorializes the dialogue between the interviewer and interviewee.

The computer system in the kiosk or other translation system can also have or access biometric software to sense and determine the biometric conditions and authenticity of the identification of the interviewee. A built in cam or camera near or on the screen can observe the interviewee and can be linked to the biometric software that can identify any signs of unusual behavior and telling body language. Many forms of biometric testing including fingerprints, body temperature and others can be integrated into the biometric software to operate the translation system and the processes of data capture, verification and printed material. Identification errors, nervousness, or hesitancy in providing information about the interviewee, can cause suspicion and signal the computer system to ask the user for more information such as the interviewee's favorite author or mother's maiden name. If the user hesitates or types in the details incorrectly, it may show misuse of a passport, bank card, identification (ID) card etc. A person who is confident in their own identity including name, address and birthday should type or say such details quickly and easily in their own language whereas someone using personal information fraudulently, such as a fake or stolen passport, driver's license or bank cards would often display errors and hesitancy that the software could pick up. The use of biometric software can be useful to detect false statements and or fraudulent use of ATM machines. When a bank card is stolen and used the thief often tries several automatic telling machines (ATMs) from which to withdraw cash, the computer system can sense the biometric conditions of the thief and send a alarm or other signal which can close down access to the ATM or credit line as well as alert the police or other local law enforcement authorities to help identify and capture the culprit.

The computer system can have or access voice recognition and communications software so that a bank or other financial institution, can ask the customer or person seeking to withdraw funds, to provide a voice recognized sample of their voice that an avatar on screen can hear and verify. The use of an avatar in ATM machines can allow a separate biometric test based on cam (camera) vision. The avatar can ask the card holder to insert their new style bank card, which can have an encrypted, scrambled and pixilated feature that when inserted in a reception slot linked to the computer system can be read and viewed. The cam (camera) in or above the screen will cross check the image of the user in front of the cam and the registered image. This correlation can be done purely by cornea scan. The application of this technology is an innovative step to combine novel benefit that hitherto has not been available to ATM machines and translation services.

This innovation can also prevent passport fraud and welfare fraud when people make false claims for benefit payments. Such fraud can cost millions of pounds or dollars annually in all countries. This innovation can greatly reduce or eradicate such fraudulent uses of bank cards and passports and help prevent false claims for welfare benefits, etc.

Communication with natives, local tribes, civilians or suspects is often difficult or impossible in war zones and translators are often sought by the enemy and executed. A virtual translator can be easier to carry around and can be very useful to military personnel. In this manner, soldiers can communicate in various tongues (languages) and reassure the locals of their peaceful intentions and help them in many ways. This will take away the advantage that the terrorists or renegade armies may currently possess. The use of biometric software by the computer system in interrogation will speed up interviews for the military and help lead to accurate information gathering more quickly and without the need for more inhuman or brutal methods of interrogation or finding out the truth.

The novel interactive electronic translation and communications process with a translation station has a solution to most of the problems discussed previously. The translation station whether fixed or mobile can contain a variety of avatars representing both sexes from all the peoples of the world. These avatars can be technically state of the art avatars with realistic human features and ethnic characteristics applicable to all races. The avatars can be placed in various and applicable settings familiar with the users or interviewee and they can appear to be helpful.

An on-screen map of the world or a visual display of national flags will assist in the identification of an interviewee's origins and language. Further sensitivity procedures and software, can highlight regionally spoken dialects.

The translation stations/kiosks can be made from composite materials, metal or other material and can feature interactive touch screens with touch control keypads bearing symbols and alphabets in most, if not all known, languages. The translation stations can also have the facility of a built in or remotely attached printer to allow interviews and interrogations to be audited and wherein encrypted responses from both the interviewer and the interviewee are obtained, verified, dated and timed. A printed document can be produced that can be signed by the patient, the suspect or a family member or representative. The document can have a space for a witness present to countersign. Statements, consent forms and declarations can also be electronically transmitted to other equipment or online services.

The computer system in the translation stations can be connected to the internet via ethernet, local are network (LAN), wireless (WiFi) and/or linked to satellite communication. Vital information can now be captured anywhere by the translation station and forwarded in a variety of ways, such as electronically or delivery by hand.

The translation station can help reduce loss of life as patients speaking different languages can communicate their problems in their own language via an intelligent avatar and assist in an accurate diagnosis being made early enough. It will also help protect doctors and surgeons from some litigation where procedures fail or result in death or patient deficiency as they can rely on a printed document which confirms awareness of risk and agreement to proceed having been given.

In immigration and border control, the translation station can assist officials in apprehending suspects and interrogating them about their travel plans and history. A border control officer can access information on site via the language translation station and to qualify statements and relevant data gleaned from the interviewee in any language.

The printer can print European, American and Asian size documents or other size documents. The printer can also print a coupon receipt for the interviewee.

In one preferred form, an interactive translation and electronic communications process is provided for use in a translation station or other places. The novel interactive electronic communications process comprises: (a) providing a central processing unit (CPU); (b) electronically recognizing a person's language from a person's conversations; (c) electronically comparing the person's language to a host language in the CPU; (d) electronically translating the person's language into the host language in the CPU if the person's language and host language are not the same; and thereafter (e) electronically transmitting audible communications in the person's language from the CPU to the person. The person can be a man, woman, child, customer, patient, traveler, refugee, immigrant, interviewee, suspected terrorist, suspected criminal, or victim.

The person's language can comprise or be electronically obtained from: voice, speech, voice message, on-line conversations, off-line conversations, verbal communications, discussions, conferences, oral responses, replies, electronic communications, and/or sound. The audible communications that are electronically transmitted to the person can comprise: inquiries, electronically synchronized speech, questions, interviews, interrogations, sounds, speech, words, dialog, discussions, menu driven communications, electronics, interactive verbal communications, or combinations of the preceding.

The CPU can comprise: a computer, laptop, desktop computer, portable computer, microprocessor, computer system, ipad, tablet computer, wireless computer, wired computer, netbook, electronic communications device, portable networking device, internet communications device, mobile phone, flip phone, camera phone, clamshell device, radio telephone, cellular phone, smart phone, tablet phone, portable media player (PMP), personal digital assistant (PDA), wireless e-mail device, handheld electronic device, mobile electronic device, or combinations of any of the preceding.

The interactive electronic communications process can further comprise: detecting biometric conditions of the person; electronically feeding, inputting or transmitting the biometric conditions of the person into the CPU; electronically comparing in the CPU the biometric conditions of the person with standardized biometric conditions from a data base; and generating an impulse if the biometric conditions of the person substantially deviate and differ from the standardized biometric conditions. The impulse can be a warning signal, verbal signal, visual signal, false reading, stop action, electronic impulse, or combinations of any of the preceding.

The biometric conditions can comprise one or more of the following: behavior patterns, temperature changes, pulse readings, eye scan, cornea scan, iris scan, retina scan, facial expressions, mouth expressions, palm reading, nostril observations, finger print analysis, teeth identification, breathing patterns, gait, rhythm, speech, voice, sweating, latency in typing, and hesitation in providing information which should be known to the person.

Advantageously, the interactive electronic communications process can also include electronically identifying the person with the CPU by electronically inputting personal information about the person from an electronic device into the CPU. The electronic device can be a camera, web cam, electronic eye, electronic lens, video camera, cam corder, face scanner, three dimensional (3D) face scanner, voice recognition device, optical reader, eye scanner, iris scanner, cornea scanner, retina scanner, blood analyzer, DNA analyzer, scanner, identification card scanner, touch screen, touch pad, screen pad, keypad, keys, and/or an electronic mouse.

The personal information of the person being electronically inputted into the CPU can be: visual information, visual surveillance, blood type, fingerprint, biological information, non-invasive data, voice, speech, DNA information, face, eyes, race, nationality, name, birthdates, address, social security number, passport number, personal identification number (PIN), passport information, driver's license, identification card information, bar code, code, mug shot, electronic information strip, hologram, photograph, personal encrypted card information, scrambled personal information, pixilated information, skin texture, nose, jaw, eyes, teeth, dental information, facial information, computerized personal information, embedded personal information, algorithm based personal information, software supported personal information, and/or combinations of any of the preceding.

Desirably, the interactive electronic communications process includes: electronically authenticating and verifying the electronic identity of the person in the CPU by electronically comparing the electronically inputted information in the CPU with electronic information about the person previously inputted and electronically stored in the CPU or downloaded into the CPU from a data base.

The interactive electronic communications process can also comprise visually displaying and viewing indicia on at least one display operatively associated with the CPU. The display can be a screen, touch screen, touchpad or monitor. The indicia can include: one or more avatars, text, words, numbers, alpha numeric images, characters, symbols, logos, designs, animation, black indicia, colored indicia, information images, videos, graphics, flags, globes, country names, country codes, country, pictures, maps, characters, cartoons, moving graphics, video clips, photographs, and/or combinations of any of the preceding.

The interactive electronic communications process can also include: electronically inputting information into the CPU through at least one inputting device operatively associated with the CPU. The inputting device can be one or more of the following: a touch screen, touch pad, screen pad, keypad, keyboard, keys, buttons, electronic mouse, audible input, Bluetooth, verbal input device, microphone, transmitter, electronic mouse, optical scanner, card reader, scanner, USB device, streaming device, audio tape, video tape, computer disc (CD), digital video disc (DVD), universal serial bus (USB) device, or flash drive.

The interactive electronic communications process can further include electronically deterring and preventing fraudulent collection and improperly receiving funds from a financial provider. Such funds can comprise: money, currency, electronic funds, welfare payments, credit, and/or wire transfers. The financial provider can be a financial institution, bank, savings and loan facility, automatic teller machine (ATM), welfare agency, government agency, currency exchange, broker, credit card company, credit union, or debit card company.

Furthermore, the interactive electronic communications process can include providing and transmitting electronic interactive communications between the CPU and the person in a place, such as: a hospital, doctor's office, trauma center, medical facility, remote area, military zone, occupied territory, terrorist area, enemy zone, border, government agency, passport control, prison, penitentiary, internment facility, police station, airport, railway station, shipping port, bus terminal, public concourse, library, museum, or combinations or variations thereof.

Moreover, the interactive electronic communications process can include conducting electronic interactive audible communications in the person's language from the CPU to the person in a translation station, such as: a mobile translation station, fixed translation station, kiosk, mobile kiosk, stationary kiosk, wheeled stand, CPU case, computer bag, information gathering area, interview area, interrogation area, communications zone, booth, private booth, stand, wheeled stand, CPU case, support surface, platform tent, tarp, collapsible structure, desk, structure, module, individual user station, metal station, composite station, multiple user kiosk, moveable support surface, computer station, cart, carrying case, brief case, suitcase and/or interactive communications module.

Preferably, the interactive electronic communications process comprises visually displaying an electronic animated avatar on the display. The avatar can be modeled from human beings of various races, nationalities and ethnic backgrounds. Desirably, the avatar has lip synchronized speech in the person's language. The speech can be synchronized and simultaneously transmitted by the CPU with the audible communications.

Advantageously, the interactive electronic communications process includes providing an electronic audit trail of the electronic translations and audible communications. The electronic audit trail can comprise one or more of the following: electronically storing said electronic translations and audible communications in the CPU; downloading the electronic translations and audible communications from the CPU into a flash drive, computer disc, backup tape, server or another CPU; printing in the person's language into the electronic translations and audible communications; printing in the host language the electronic translations and audible communications; printing an encrypted version of the electronic translations and audible communications; downloading an encrypted version of the electronic translations and audible communications; electronically establishing a log of the electronic translations and audible communications; signing a printed version of the translations and audible communications; and witnessing a printed version or printed document(s) of the translation and communications.

In another preferred form, the interactive electronic communications process comprises: providing a central processing unit (CPU) for interaction between a host comprising an interviewer and a person comprising an interviewee; electronically inputting information into the CPU through at least one imputing device operatively associated with the CPU; visually displaying and viewing indicia on at least one display operatively associated with the CPU; electronically recognizing the person's language from a person's communications; electronically comparing the person's language to the host language in the CPU; electronically translating the person's language into the host language in the CPU if the person's language is different than the host language; transmitting electronic communications in the person's language from the CPU to the interviewee; and providing an audit trail by printing the electronic translations and the electronic communications in both the host language and the person's language on a printer hard wired or operatively connected by wireless to the CPU.

A more detailed explanation of the invention is provided in the following detailed descriptions and appended claims taken in conjunction with the accompanying drawings.

BRIEF DESCRIPTION OF THE DRAWINGS

FIG. 1 is a diagrammatic view of an interactive translation and electronic communications process with a translation station in an open position in accordance with principles of the present invention.

FIG. 2 is a reduced perspective view of the translation station in a closed position.

FIG. 4 is a diagrammatic view of an interactive translation and electronic communications process with a further translation station in a hospital in accordance with principles of the present invention.

FIG. 5 is a diagrammatic view of a variation of the translation station for use in an interactive translation and electronic communications process in accordance with principles of the present invention.

DESCRIPTION OF THE INVENTION

Figure 3:
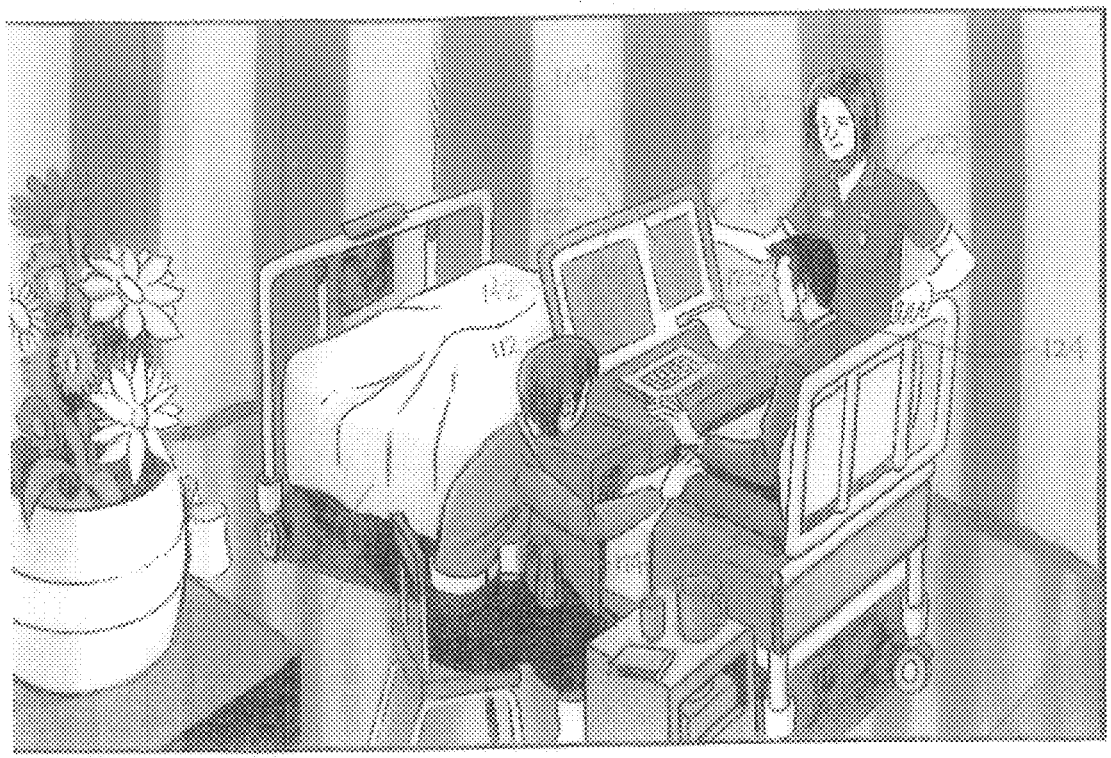
FIG. 3 is a diagrammatic view of an interactive translation and electronic communications process with another translation station in a hospital in accordance with principles of the present invention.

The following is a detailed description and explanation of the preferred embodiments of the invention and best modes for practicing the invention.

As shown in FIG. 1 of the drawings, an interactive electronic translation and communications process 100 is provided for use in a translation station 102 or other places 104. The interactive electronic communications process can comprise providing a computer system 106 with a printer 108, at least one inputting device 110, and one or dual displays 112 and 114 which are operatively connected by hard wiring or wireless to a central processing unit (CPU) 116 for interaction between a host 118 (FIG. 3) comprising an interviewer 120 and a person 122 comprising an interviewee 124. The interviewer can be: an individual, nurse, physician, dentist, medical technician, dental technician, administrative assistant, policeman, detective, interrogator, soldier, military personnel, bank official, security personnel, airport official, transportation personnel, government official, border patrol, immigration officer; teacher, school official, university or college administrator, or representative of a company.

The person comprising the interviewee can be: a man, woman, child, customer, patient, traveler, suspected terrorist, suspected criminal, refugee, immigrant and/or victim.

The CPU can be: a computer, laptop computer, desktop computer, portable computer, microprocessor, tablet computer, wireless computer, wired computer, netbook, internet communications device, portable networking device, electronic communications device, and/or combinations of any of the preceding.

The dual displays can comprise side-by-side laterally spaced displays with each display comprising a screen, touch screen, touchpad, monitor and combinations of any of the preceding.

Each inputting device can be one or more of the following: a keypad, retractable keypad, screen pad, touch pad, keyboard, retractable keyboard, keys, buttons, and electronic mouse.

The interactive electronic communications process can comprise: electronically inputting information from the person comprising the interviewee in the interviewee's language through the inputting device to the CPU; electronically translating the inputting information in the CPU from the interviewee into the language of the host comprising the interviewer if the interviewee's language is different than the interviewer's language; visually displaying and electronically transmitting an electronic animated avatar 125 (FIG. 1) from the CPU on one of the dual displays with lip synchronized speech in the interviewee's language, the avatar being modeled from human beings from the interviewee's country; visually displaying electronic visual communications from the interviewer to the interviewee in the interviewee's language on one of the dual displays; and providing an audit trail by printing the electronic visual communications from the printer in both the interviewee's language and the interviewer's language.

Such visual communications can comprise indicia comprising one or more of the following: text, words, numbers, alpha numeric images, logos, designs, images, videos, video clips, graphics, flags, countries, maps, globe, country names, country codes, animation, black indicia, colored indicia, pictures, information, characters, cartoons, graphics, moving graphics, and/or photographs.

The computer system can include: an interviewee's inputting device 126 (FIG. 1) and an interviewer's inputting device 128. The interviewee's inputting device can be separate from the interviewer's inputting device. The computer system can further include at least one speaker 130 and an audible transmitter 132 or microphone 134. The speaker can be an external speaker, internal speaker, headphone jack, headphones, earplug jack and/or earplugs.

The translation station can comprise a mobile translation station 136 with a mobile case 136 (FIG. 1) having carry handles 138 and 139, collapsible struts 140, a hinged back lid 145 which accommodates one or more computer screens 142 and 144 providing displays. The hinged back lid 145 can be closed to a closed hinged position as shown in FIG. 2. The mobile translation station can have an internet connection 146 (FIG. 1) with LAN and/or WiFi. The right screen 144 can display a multi-lingual dialogue box 148. The mobile translation station can further have battery storage 148 under the built-in printer 108. The mobile translation station can further have a power cable socket 152 and a power cord 153. The mobile translation station can also have a retractable paper cartridge 154 on the left side to feed paper to the printer and has a printer outlet 156 on the right side to discharge the printed paper documents 158. The left screen 142 can display one or more avatars 125. The inputting devices can comprise dual retraceable key pads 160 or multi-lingual touch screens 162. The mobile case can be supported by a support surface 164 of a desk 166.

In FIGS. 3 and 4, the mobile healthcare medical translation station comprises a slidable tray 168 providing a slidable support surface over a bed 169 in a hospital to support the inputting device providing a keyboard 170 or touch screen. The tray can slide on an invented U-shaped support 172 with downwardly extending legs 176. The paper outlet 178 can be positioned below the right screen.

In FIG. 5, the mobile translation station includes a wheeled cart 180 with a bottom shelf 181 to support paper 182. The wheeled cart has legs 183 and caster wheels 184. The paper outlet 185 can be located below the inputting device comprising a touchpad or keypad.

Figure 6:
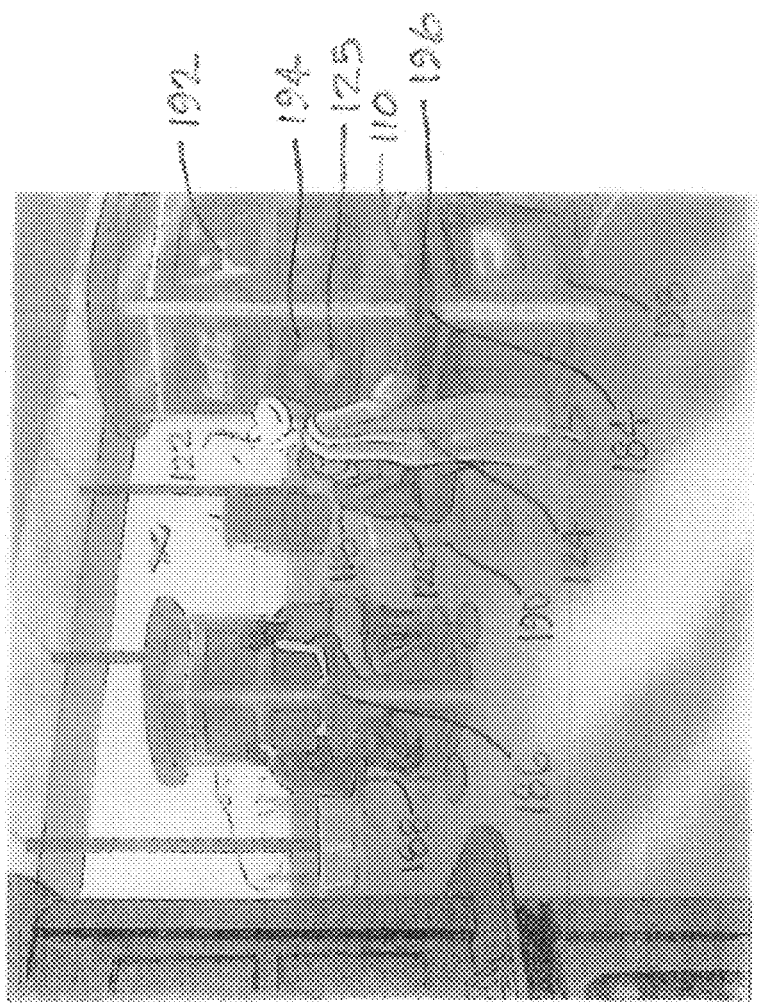
FIG. 6 is a diagrammatic view of an interactive translation and electronic communications process with carousals comprising translation stations in a airport in accordance with principles of the present invention.

FIG. 6 illustrates fixed airport translation stations 184 comprising multipanel carousels 186 with stools 188 and chairs 190 in an airport. The carousels be fixed or rotate and can have an overhead display screen 192 and lower display screens 194 at about eye level. The carousel can have horizontal planar or flat support surfaces 196 for the inputting devices. The carousels can comprise a tower and can also have storage bins or compartments 198 below the support surface, as well as an automatic teller machine (ATM). Such carousels can also be used in transportation terminals, such as bus terminals, railway stations, ports, ships or museums, libraries and government buildings.

Figure 7:
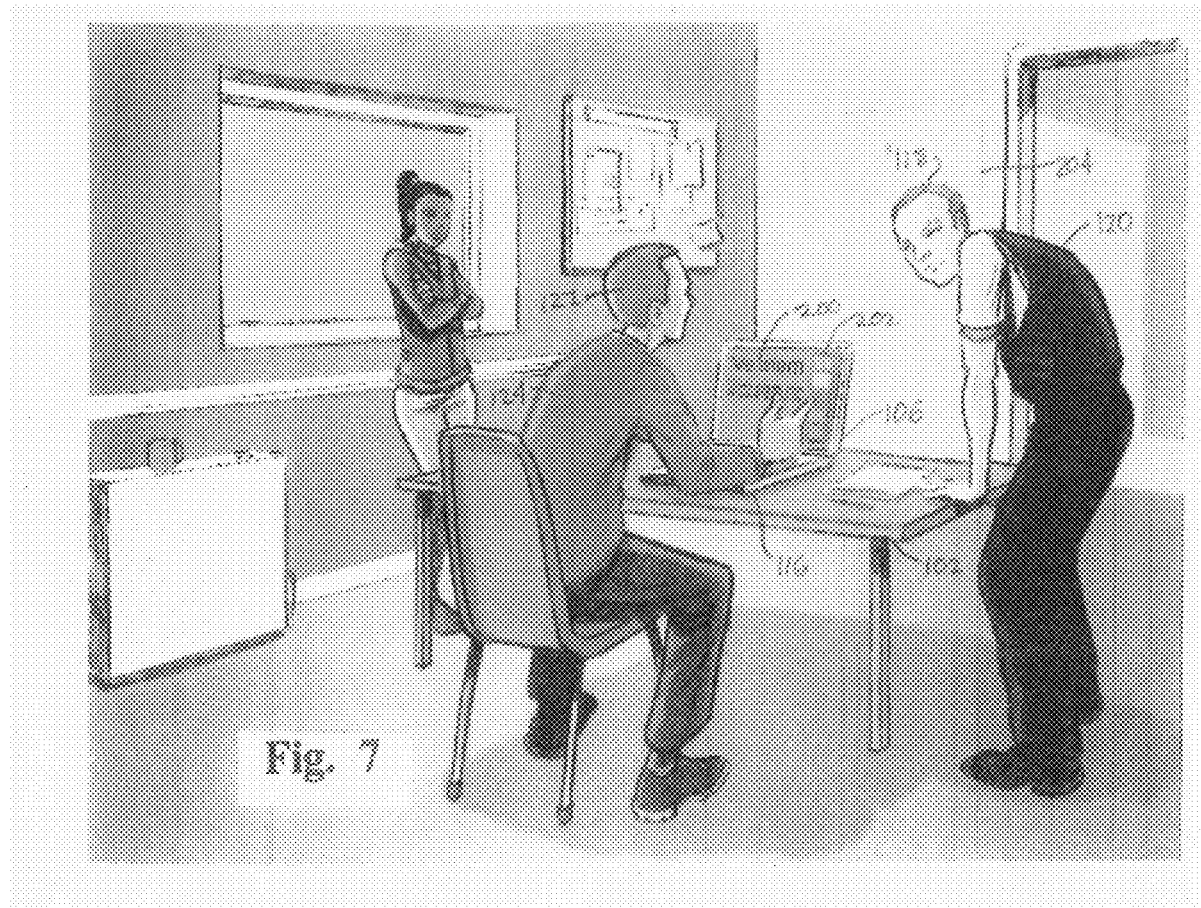
FIG. 7 is a diagrammatic view of an interactive translation and electronic communications process with yet another translation station in an interview room in accordance with principles of the present invention.

FIG. 7 illustrates the translation station with a touch screen 200 having haptics providing touch buttons 202 in an interview room 204.

Figure 8:
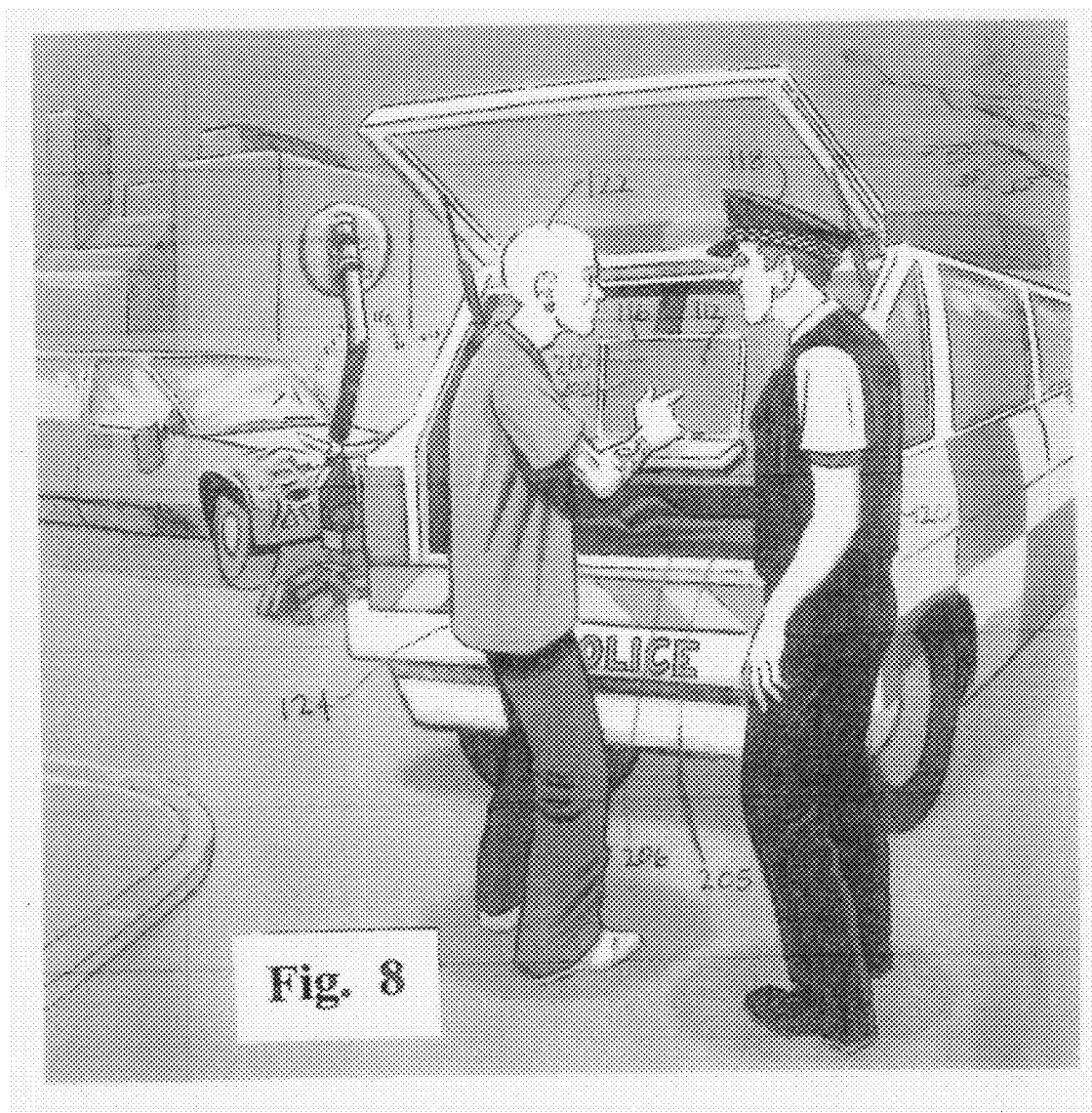
FIG. 8 is a diagrammatic view of an interactive translation and electronic communications process with still a further translation station being used by the police in accordance with principles of the present invention.

FIG. 8 illustrates a law enforcement mobile translation station 205 being used by the police on a mobile support surface 206 of an automobile 208, such a police van or wagon, to interview a witness or a victim in an automobile (car) accident. The mobile translation station can produce or print statements or declarations that are being translated, memorialized and witnessed as evidence.

Figure 9:
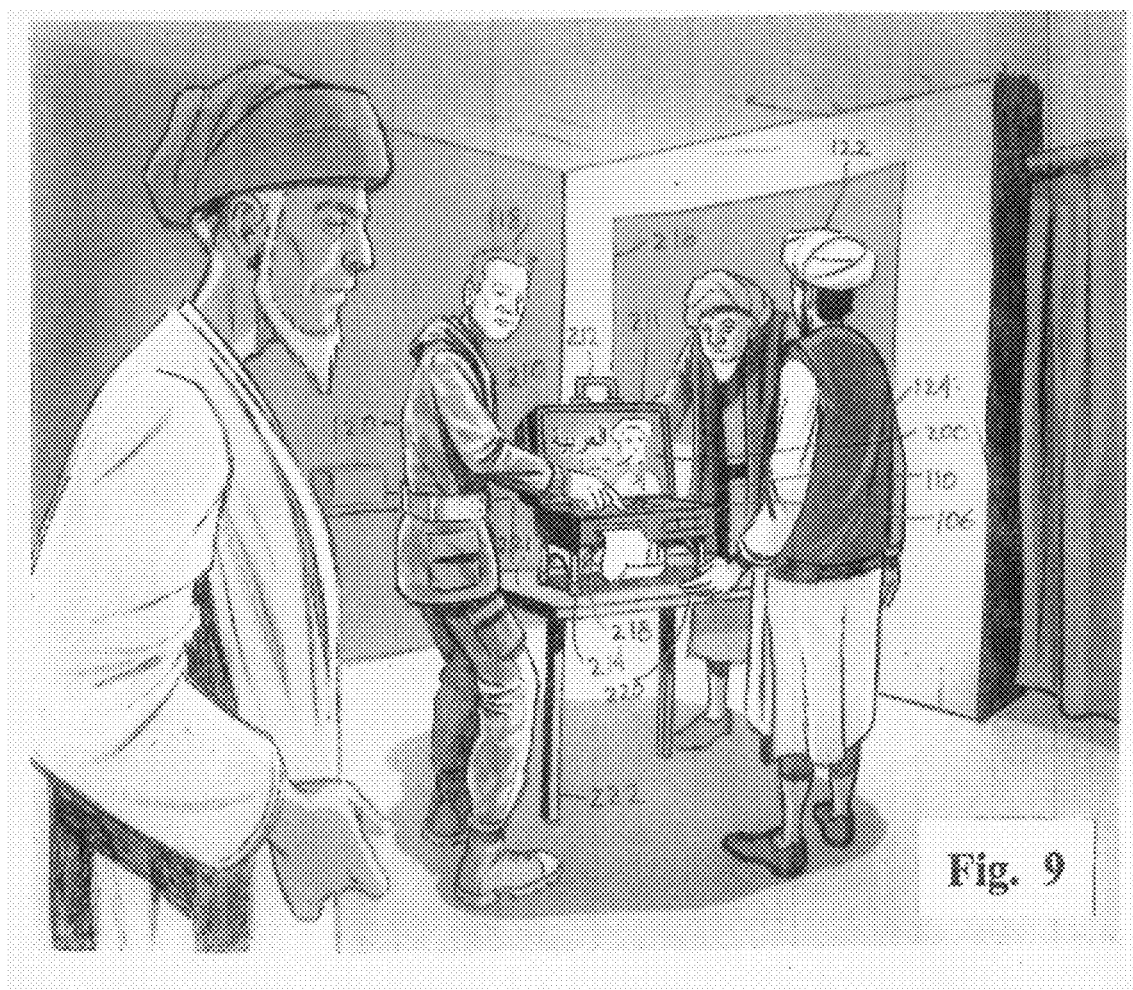
FIG. 9 is a diagrammatic view of an interactive translation and electronic communications process with another translation station being used in an interrogation room by the military in accordance with principles of the present invention.

FIG. 9 illustrates a mobile military translation station 210 comprising a mobile case 211 with a carrying handles 212 and retractable legs 214 being used in an interrogation room 216 by military personnel (soldier). The mobile case can have a paper outlet 218 positioned below the inputting device comprising a keyboard, keypad or touch screen. The mobile case can be supported by a table 220 with a horizontal support surface 221 and downwardly depending vertical legs 222 of a desk. The mobile translation station can also be used in a war zone. The mobile translation station can comprise a remote unit which is battery or mains powered and connected to the internet via a roaming device and or satellite. The ability to communicate in any language or a local dialect can save time and lives. This can also be beneficial to the military in pre-deployment training of troops, field medicine and a campaign to win hearts and minds of civilians in the militarized zone.

The mobile translation station can be produced in a rugged mobile case that has foldaway legs and supports to allow use in uneven terrain or to be opened up like a suitcase or briefcase. The back of the mobile case can contain a screen linked to a keypad in the other section. There can be a printer link or not as preferred. The screen can present avatars in the likeness of the local communities where the action is taking place. In Afghanistan, for example the avatars will look local and be wearing local tribal clothing and headgear (turbans). The avatar will feature the facial characteristic of the peoples and can be programmed to speak in many local dialects.

The interactive electronic communications process can also comprise: electronically inputting questions and responses from the interviewer through the interviewer's inputting device into the CPU; electronically visually displaying the interviewer's questions and responses in the interviewee's language on one of the dual displays for viewing by the interviewee; electronically inputting the information from the interviewee and replies from the interviewee to the questions and response from the interviewer on the interviewee's inputting device; and simultaneously electronically displaying the replies from the interviewee to the questions and responses of the interviewer on one of the dual displays in the interviewee's language and on the other dual display in the interviewer's language.

The interactive electronic communications process can further comprise: conducting electronic audible communications between the interviewee and the interviewer in the interviewee's language by: audibly inputting information and audible communications from the interviewee into the audible transmitter or microphone; electronically translating the audible inputted information and audible communications from the interviewee into the interviewer's language on the CPU; and audibly communicating questions and responses from the interviewer through the speaker of the computer system to the interviewee in the interviewee's language.

Furthermore, the interactive electronic communications process can comprise transporting, supporting and operating the computer system in or on a translation station. The translation station can be: a portable carrying case, a mobile case, a briefcase, a case with input slots for ingress and egress of one or more retractable inputting devices, a hinged case having a base and a pivotable lid providing a top, a case with a paper output slot, a case with a paper tray slot, a case with extendable and retractable legs, a case with a collapsible struts, a case with a handle, a wheeled stand, a mobile kiosk tray, a slidable tray, a cart, a moveable support surface, briefcase, suitcase and combinations of any of the preceding.

Moreover, the interactive electronic communications process can comprise electronically identifying the person comprising the interviewee on the CPU by electronically inputting personal information about the interviewee from an electronic device into the CPU; and electronically authenticating and verifying the electronic identity of the person in the CPU by electronically comparing the electronically inputted information in the CPU with electronic information about the person previously inputted and electronically stored in the CPU or downloaded into the CPU from a data base. The personal information can include one or more of the following: visual information, visual surveillance, blood type, fingerprint, biological information, non-invasive data, voice, speech, DNA information, face, eyes, race, nationality, name, birthdate, address, social security number, passport number, personal identification number (PIN), passport information, driver's license, identification card information, bar code, code, mug shot, electronic information strip, hologram, photograph, personal encrypted card information, scrambled personal information, pixilated information, skin texture, nose, jaws, eyes, teeth, dental information, facial information, computerized personal information, embedded personal information, algorithm based personal information, and/or software supported personal information.

The electronic device for electronically inputting personal information about the interviewee into the CPU can be one or more of the following: a camera, web cam, electronic eye, electronic lens, video camera, cam corder, face scanner, three dimensional (3D) face scanner, voice recognition device, optical reader, eye scanner, iris scanner, cornea scanner, retina scanner, blood analyzer, DNA analyzer, scanner, identification card scanner, touch screen, touch pad, screen pad, keypad, keys, and/or electronic mouse.

Also, the interactive electronic communications process can comprise: detecting biometric conditions of the person; electronically feeding, inputting or transmitting the biometric conditions of the person into the CPU; electronically comparing in the CPU the biometric conditions of the person with standardized biometric conditions from a data base; generating an impulse from the CPU if the biometric conditions of the person substantially differ from the standardized biometric conditions; and transmitting electronic interactive communications from the CPU to the interviewee in a place, such as: a hospital, doctor's office, trauma center, medical facility, remote area, military zone, occupied territory, terrorist area, enemy zone, border, government agency, passport control, prison, penitentiary, internment facility, police station, interview room, interrogation room, airport, railway station, shipping port, bus terminal, public concourse, library, museum, financial institution, bank, savings and loan facility, automatic teller machine (ATM), welfare agency, government agency, currency exchange, broker, credit card company, credit union, and/or debit card company.

The biometric conditions being detected can comprise: behavior patterns, temperature changes, pulse readings, eye scan, cornea scan, iris scan, retina scan, facial expressions, mouth expressions, palm reading, nostril observations, finger print analysis, teeth identification, breathing patterns, gait, rhythm, speech, voice, sweating latency in typing, hesitation in providing information which should be known to the interviewee and combinations of any of the proceeding.

The impulse from the CPU can comprise: a warning signal, verbal signal, visual signal, false reading, stop action, electronic impulse, or combinations of the preceding.

The steps occurring in, by or from the CPU which are described in this application, can be assisted or enhanced with one or more publicly available computer programs or software, which are downloadable to the CPU from a computer disc, flash drive, or accessible through the internet or from another electronic device.

The kiosks or other translations stations can be made from composite materials, plastic, metal, such as stainless steel or aluminum, or other materials. The kiosks can be fixed or mobile. Desirably, the kiosk can be mobile and in a ruggedized case for use in hostile territory or conditions such as for the military. Furthermore, the kiosks can have one or more screens on one or more sides to allow a tower effect with four sided access. The kiosks can also be individual user stations.

The kiosks or other translations stations can have overhead displays or upper screens for advertising space in airport lounges and other public places. The additional displays or screens can be positioned to display advertising and to attract revenues from sale of such space. Such additional displays or screens can be most used in public areas in places where the user does not speak the native language and seeks translation services from the online avatars. This information can be useful for travelers seeking assistance with transport, accommodation and or entertainment. Such information can also be useful for travelers and others who may need medical assistance for themselves or a member of their party. Public translation stations or kiosks can also be useful for general public concourses and libraries, museums etc. Kiosks or other translation stations can also be useful in official areas and can be operated by an officer or a doctor, or their assistants.

The interactive electronic communications process can provide an encrypted audit trail linked to a printer wherein a print out consent form can be produced for the patient, suspect, victim or other interviewee to sign. To this end, the kiosk or other translation station, can have an on board printer to deliver printed documents of various sizes. Alternatively, the CPU in the kiosk or other translation station can be wired or connected by wireless to a small receipt printer linked to a larger bank of printers in a controlled area where the documents can be printed. If in a controlled and supervised official area, the receipt can bear the encrypted code to match the print out documents. In areas of general public use, the user can enter an encryption pin code and the produced receipt can be exchanged at the printing desk area manned by staff. Verification can be requested wherein sensitive information is involved between the two points.

The translation stations can be either fixed or mobile to preview an interactive facility for interviews and interrogations to be carried out between at least two parties speaking at least in two different languages. The process can be managed by virtual characters (avatars) realistically created to represent ethnic looks from around the globe. The avatars can be lip synchronized to deliver messages in many or all languages and can guide the users and interviewee through a series of menu driven questions and answers.

Translation software for various languages and linguistics as well as voice and dialect recognition software can be used in conjunction with the computer system to help manage and interpret sentences and phrases at high speed. When used in combination with integrated biometric software, the translation stations can also provide for the detection and online analysis of behavioral inconsistencies. The built in printer can deliver an accurate printout and/or encrypted record of all conversations, declarations and statements that can be submitted as evidence in court or any other arena of jurisdiction or concern.

The mobile and fully transportable unit means that the system can be used locally to individuals at the roadside, bedside or other location where needed and when linked to a global positioning system (GPS) and the internet can deliver translated data immediately to wherever required.

The invention process and translation station is new and of great value to the law enforcement officers, medical personnel, the military, border control units, and security personnel at airports, railroad stations, bus terminals, etc. and others.

Among the many advantages of the interactive electronic translation and communications process are:

1. Superior performance.
2. No waiting for translators to arrive.
3. Audit trails carried out locally.
4. Useful in emergencies, as well as law enforcement, security, investigations and customer identification.
5. Convenient.
6. User friendly.
7. Reliable.
8. Readily transportable.
9. Light weight.
10. Portable.
11. Simple to operate.
12. Easy to use.
13. Durable.
14. Economical.
15. Attractive.
16. Efficient.
17. Effective.

Although embodiments of the invention have been shown and described, it is to be understood that various modifications, substitutions, and rearrangements of equipment, parts, components, and/or process (method) steps, as well as other uses of the interactive electronic translation and communications process can be made by those skilled in the art without departing from the novel spirit and scope of this invention.

What is claimed is:

1. An interactive electronic communications process for use in a translation station or other places, comprising:
   providing a central processing unit (CPU) selected from the group consisting of a computer, laptop, desktop computer, portable computer, microprocessor, computer system, iPad, tablet computer, wireless computer, wired computer, netbook, electronic communications device, portable networking device, internet communications device, mobile phone, flip phone, camera phone, clamshell device, radio telephone, cellular phone, smart phone, tablet phone, portable media player (PMP), personal digital assistant (PDA), wireless e-mail device, handheld electronic device, mobile electronic device, and combinations of any of the preceding;
   electronically recognizing a person's language from a person's conversations selected from the group consisting of voice, speech, voice message, on-line conversations, off-line conversations, verbal communications, discussions, conferences, oral responses, replies, electronic communications, and sound;
   electronically comparing the person's language to a host language in the CPU;
   electronically translating the person's language into the host language in the CPU if the person's language and host language are not the same;
   electronically transmitting audible communications in the person's language from the CPU to the person, the audible communications selected from the group consisting of inquiries, electronically synchronized speech, questions, interviews, interrogations, sounds, speech, words, dialog, discussions, menu driven communications, electronics, interactive verbal communications, and combination thereof; and
   providing an audit trail by printing said electronic translations and said electronic communications in both the host language and the person's language on a printer hard wired or operatively connected by wireless to the CPU.

2. An interactive electronic communications process in accordance with claim 1 including:
   detecting biometric conditions of the person;
   the biometric conditions being selected from the group consisting of behavior patterns, temperature changes, pulse readings, eye scan, cornea scan, iris scan, retina scan, facial expressions, mouth expressions, palm reading, nostril observations, finger print analysis, teeth identification, breathing patterns, gait, rhythm, speech, voice, sweating, latency in typing, hesitation in providing information which should be known to the person, and combinations of any of the preceding;
   electronically feeding, inputting or transmitting the biometric conditions of the person into the CPU;
   electronically comparing in the CPU the biometric conditions of the person with standardized biometric conditions from a data base;
   generating an impulse if the biometric conditions of the person substantially deviate and differ from the standardized biometric conditions; and
   said impulse being selected from the group consisting of a warning signal, verbal signal, visual signal, false reading, stop action, electronic impulse, and combinations thereof.

3. An interactive electronic communications process in accordance with claim 1 including:
   electronically identifying the person with the CPU by electronically inputting personal information about the person from an electronic device into the CPU;
   said personal information being selected from the group consisting of visual information, visual surveillance, blood type, fingerprint, biological information, non-invasive data, voice, speech, DNA information, face, eyes, race, nationality, name, birthdate, address, social security number, passport number, personal identification number (PIN), passport information, driver's license, identification card information, bar code, code, mug shot, electronic information strip, hologram, photograph, personal encrypted card information, scrambled personal information, pixilated information, skin texture, nose, jaw, eyes, teeth, dental information, facial information, computerized personal information, embedded personal information, algorithm based personal information, software supported personal information, and combination thereof;
   said electronic device being selected from the group consisting of a camera, web cam, electronic eye, electronic lens, video camera, cam corder, face scanner, three dimensional (3D) face scanner, voice recognition device, optical reader, eye scanner, iris scanner, cornea scanner, retina scanner, blood analyzer, DNA analyzer, scanner, identification card scanner, touch screen, touch pad, screen pad, keypad, keys, and electronic mouse; and
   the person is selected from the group consisting of a man, woman, child, customer, patient, traveler, refugee, immigrant, interviewee, suspected terrorist, suspected criminal, and victim.

4. An interactive electronic communications process in accordance with claim 3 including:
   electronically authenticating and verifying the electronic identity of the person in the CPU by electronically comparing the electronically inputted information in the CPU with electronic information about the person previously imputed and electronically stored in the CPU or downloaded into the CPU from a data base.

5. An interactive electronic communications process in accordance with claim 1 including:
   visually displaying and viewing indicia on at least one display operatively associated with the CPU;
   said display selected from the group consisting of a screen, touch screen, touchpad and monitor; and
   said indicia selected from the group consisting of one or more avatars, text, words, numbers, alpha numeric images, characters, symbols, logos, designs, animation, black indicia, colored indicia, information images, videos, graphics, flags, globes, country names, country codes, country, pictures, maps, characters, cartoons, moving graphics, video clips, photographs, and combinations of any of the preceding.

6. An interactive electronic communications process in accordance with claim 1 including:
   electronically inputting information into the CPU through at least one imputing device operatively associated with the CPU;
   said inputting device selected from the group consisting of a touch screen, touch pad, screen pad, keypad, keyboard, keys, buttons, electronic mouse, audible input, Bluetooth, verbal input device, microphone, transmitter, electronic mouse, optical scanner, card reader, scanner, USB device, streaming device, audio tape, video tape, computer disc (CD), digital video disc (DVD), universal serial bus (USB) device, and flash drive.

7. An interactive electronic communications process in accordance with claim 1 including:
   electronically deterring and preventing fraudulent collection and improperly receiving funds from a financial provider;
   said funds selected from the group consisting of money, currency, electronic funds, welfare payments, credit, wire transfers, and combination thereof; and
   said financial provider selected from the group consisting of a financial institution, bank, savings and loan facility, automatic teller machine (ATM), welfare agency, government agency, currency exchange, broker, credit card company, credit union, and debit card company.

8. An interactive electronic communications process in accordance with claim 1 including providing and transmitting electronic interactive communications between the CPU and the person in a place selected from the group consisting of a hospital, doctor's office, trauma center, medical facility, remote area, military zone, occupied territory, terrorist area, enemy zone, border, government agency, passport control, prison, penitentiary, internment facility, police station, interview room, interrogation room, airport, railway station, shipping port, bus terminal, public concourse, library, and museum.

9. An interactive electronic communications process in accordance with claim 1 including conducting electronic interactive audible communications in the person's language from the CPU to the person in a translation station selected from the group consisting of a mobile translation station, fixed translation station, kiosk, mobile kiosk, stationary kiosk, wheeled stand, CPU case, computer bag, information gathering area, interview area, interrogation area, communications zone, booth, private booth, stand, wheeled stand, CPU case, support surface, platform tent, tarp, collapsible structure, desk, structure, module, individual user station, metal station, composite station, multiple user kiosk, moveable support surface, computer station, cart, carrying case, briefcase, suitcase, interactive communications module, and combinations of any of the preceding.

10. An interactive electronic communications process in accordance with claim 1 including:
   visually displaying an electronic animated avatar on the display;
   said avatar having lip synchronized speech in the person's language;
   said speech being synchronized and simultaneously transmitted by the CPU with said audible communications; and
   said avatar being modeled from human beings of various races, nationalities and ethnic backgrounds.

11. An interactive electronic communications process in accordance with claim 1 including:
   said audit trail including providing an electronic audit trail of said electronic translations and audible communications;
   said electronic audit trail selected from the group consisting of electronically storing said electronic translations and audible communications in the CPU;
   downloading the electronic translations and audible communications from the CPU into a flash drive, computer disc, backup tape, server or another CPU;
   printing an encrypted version of the electronic translations and electronic communications;
   downloading an encrypted version of the electronic translations and electronic communications;
   electronically establishing a log of the electronic translations and electronic communications;
   signing a printed version of the electronic translations and electronic communications; and
   witnessing a printed version of the electronic translations and electronic communications.

12. An interactive electronic communications process for use in a translation station or other places, comprising:
   providing a central processing unit (CPU) for interaction between a host comprising an interviewer and a person comprising an interviewee;
   said CPU selected from the group consisting of a computer, laptop, desktop computers, portable computer, microprocessor, computer system, iPad, tablet computer, wireless computer, wired computer; netbook, electronic communications device, portable networking device, internet communications device, camera phone, mobile phone, flip phone, clamshell device, radio telephone, cellular phone, smart phone, tablet phone, portable media player (PMP), personal digital assistant (PDA), wireless e-mail device, handheld electronic device, mobile electronic device, and combinations of any of the preceding;
   electronically inputting information into the CPU through at least one imputing device operatively associated with the CPU;
   said inputting device selected from the group consisting of a touch screen, touch pad, screen pad, keypad, keyboard, keys, buttons, electronic mouse, audible input, bluetooth, verbal input device, microphone, transmitter, electronic mouse, optical scanner, card reader, scanner, streaming device, audio tape, video tape, computer disc (CD), digital video disc (DVD), universal serial bus (USB) device, and flash drive;
   visually displaying and viewing indicia on at least one display operatively associated with the CPU;
   said display selected from the group consisting of a screen, touch screen, touchpad and monitor;
   said indicia selected from the group consisting of one or more avatars, text, words, numbers, alpha numeric images, symbols, logos, designs, animation, black indicia, colored indicia, information images, videos, graphics, flags, globes, country names, country codes, country pictures, maps, characters, cartoons, graphics, moving graphics, video clips, photographs, and combinations of any of the preceding;
   electronically recognizing the person's language from a person's communications selected from the group consisting of voice, speech, voice messages, on-line communications, off-line conversations, verbal communications, discussions, conferences, responses, replies, electronic communications, and sound;
   electronically comparing the person's language to the host language in the CPU;
   electronically translating the person's language into the host language in the CPU if the person's language is different than the host language;
   transmitting electronic communications in the person's language from the CPU to the interviewee, said electronic communications selected from the group consisting of electronically synchronized speech, visual communications, questions, responses, interrogations, interviews, sound, speech, words, discussions, electronic menu driven communications, interactive verbal communications and combinations thereof; and
   providing an audit trail by printing said electronic translations and said electronic communications in both the host language and the person's language on a printer hard wired or operatively connected by wireless to the CPU.

13. An interactive electronic communications process in accordance with claim 12 including:
   detecting biometric conditions of the person comprising the interviewee;
   the biometric conditions being selected from the group consisting of behavior patterns, temperature changes, pulse readings, eye scan, cornea scan, iris scan, retina scan, facial expressions, mouth expressions, palm readings, nostril observations, finger print analysis, teeth identification, breathing patterns, gait, rhythm, speech, voice, sweating, latency in typing, hesitation in providing information which should be known to the person, and combinations of any of the preceding;
   electronically feeding, inputting or transmitting the biometric conditions of the person into the CPU;
   electronically comparing in the CPU the biometric conditions of the person with standardized biometric conditions from a data base;
   generating an impulse if the biometric conditions of the person substantially deviate and differ from the standardized biometric conditions; and
   said impulse being selected from the group consisting of a warning signal, verbal signal, visual signal, false reading, stop action, electronic impulse, and combinations thereof.

14. An interactive electronic communications process in accordance with claim 12 including:
   electronically identifying the interviewee with the CPU;
   said identifying comprising electronically inputting personal information about the interviewee from an electronic device into the CPU;
   said personal information being selected from the group consisting of visual information, visual surveillance, blood type, fingerprint, biological information, non-invasive data, voice, speech, DNA information, face, eyes, race, nationality, name, birthdate, address, social security number, passport number, personal identification number (PIN), passport information, driver's license, identification card information, bar code, code, mug shot, electronic information strip, hologram, photograph, personal encrypted card information, scrambled personal information, pixilated information, skin texture, nose, jaw, eyes, teeth, dental information, facial information, computerized personal information, embedded personal information, algorithm based personal information, software supported personal information, and combinations thereof;

said electronic device being selected from the group consisting of a camera, web cam, electronic eye, electronic lens, video camera, cam corder, face scanner, three dimensional (3D) face scanner, voice recognition device, optical reader, eye scanner, iris scanner, cornea scanner, retina scanner, blood analyzer, DNA analyzer, scanner, identification card scanner, touch screen, touch pad, screen pad, keypad, keys, and electronic mouse; and the interviewee is selected from the group consisting of a man, woman, child, customer, patient, traveler, refugee, immigrant, suspected terrorist, suspected criminal and victim;

the interviewer is selected from the group consisting of a doctor, physician, nurse, dentist, hospital staff, medical technician, dental technician, administrative assistant, policeman, detective, law enforcement official, interrogator, soldier, military personnel, bank official, security personnel, airport official, transportation personnel, government official, border control guard, immigration officer; teacher, school official, university of college administrator, or representative of a company, and an individual;

electronically authenticating and verifying the electronic identity of the person in the CPU by electronically comparing the electronically inputted information in the CPU with electronic information about the person previously imputed and electronically stored in the CPU or downloaded into the CPU from a data base;

transmitting electronic interactive communications from the CPU to the interviewee in a place selected from the group consisting of a hospital, doctor's office, trauma center, medical facility, remote area, military zone, occupied territory, terrorist area, enemy zone, border, government agency, passport control, prison, penitentiary, internment facility, police station, interview room, interrogation room, airport, railway station, shipping port, cruise ship, bus terminal, public concourse, library, museum, financial institution, bank, savings and loan facility, automatic teller machine (ATM), welfare agency, government agency, currency exchange, broker, credit card company, credit union, and debit card company.

15. An interactive electronic communications process in accordance with claim 12 including:

visually displaying an electronic animated avatar on the display;

said avatar having lip synchronized speech in the person's language;

said speech being synchronized and simultaneously transmitted by the CPU with said electronic communications;

said avatar being modeled from human beings of various races, nationalities and ethnic backgrounds; and conducting and transmitting electronic interactive audible communications in the person's language from the CPU to the person in a translation station selected from the group consisting of a mobile translation station, fixed translation station, kiosk, mobile kiosk, stationary kiosk, wheeled stand, CPU case, computer bag, information gathering area, interview area, interrogation area, communications zone, booth, private booth, stand, wheeled stand, CPU case, support surface, platform tent, tarp, collapsible structure, desk, structure, module, individual user station, metal station, composite station, multiple user kiosk, moveable support surface, computer station, cart, carrying case, interactive communications module, and combinations of any of the preceding.

16. An interactive electronic communications process in accordance with claim 12 including visually displaying the indicia on multiple displays positioned above each other, in vertical alignment, side by side, or in lateral alignment.

17. An interactive electronic communications process for use in a translation station or other places, comprising:

providing a computer system with a printer, at least one inputting device, and dual displays operatively connected by hard wiring or wireless to a central processing unit (CPU) for interaction between a host comprising an interviewer and a person comprising an interviewee, said CPU selected from the group consisting of a computer, laptop computer, desktop computer, portable computer, microprocessor, tablet computer, wireless computer, wired computer, netbook, internet communications device, portable networking device, electronic communications device, and combinations of any of the preceding;

said dual displays comprising side-by-side laterally spaced displays selected from the group consisting of a screen, touch screen, touchpad, monitor and combinations of any of the preceding;

each inputting device selected from the group consisting of a keypad, retractable keypad, screen pad, touch pad, keyboard, retractable keyboard, keys, buttons, and electronic mouse;

electronically inputting information from the person comprising the interviewee in the interviewee's language through the inputting device to the CPU;

electronically translating the inputting information in the CPU from the interviewee into the language of a host comprising an interviewer if the interviewee's language is different than the interviewer's language;

visually displaying and electronically transmitting an electronic animated avatar from the CPU on one of the dual displays with lip synchronized speech in the interviewee's language, the avatar being modeled from human beings from the interviewee's country;

visually displaying electronic visual communications from the interviewer to the interviewee in the interviewee's language on one of the dual displays, said visual communications comprising indicia selected from the group consisting of one or more text, words, numbers, alpha numeric images, logos, designs, images, videos, video clips, graphics, flags, countries, maps, globe, country names, country codes, animation, black indicia, colored indicia, pictures, information, characters, cartoons, graphics, moving graphics, photographs, and combinations of any of the preceding; and providing an audit trail by printing said electronic visual communications from the printer in both the interviewee's language and the interviewer's language.

18. An interactive electronic communications process in accordance with claim 17 wherein:

the computer system includes an interviewee's inputting device and an interviewer's inputting device, the interviewee's inputting device being separate from the interviewer's inputting device; and the process includes;

electronically inputting questions and responses from the interviewer through the interviewer's inputting device into the CPU;

electronically visually displaying the interviewer's questions and responses in the interviewee's language on one of the dual displays for viewing by the interviewee;

electronically inputting the information from the interviewee and replies from the interviewee to the questions and response from the interviewer on the interviewee's inputting device; and simultaneously electronically displaying the replies from the interviewee to the questions and responses of the interviewer on one of the dual displays in the interviewee's language and on the other dual display in the interviewer's language.

19. An interactive electronic communications process in accordance with claim 17 wherein:

the computer system includes at least one speaker and an audible transmitter or microphone, the speaker being selected from the group consisting of an external speaker, internal speaker, headphone jack, headphones, earplug jack and earplugs;

the process includes conducting electronic audible communications between the interviewee and the interviewer in the interviewee's language by audibly inputting information and audible communications from the interviewee into the audible transmitter or microphone;

electronically translating the audible inputted information and audible communications from the interviewee into the interviewer's language on the CPU; and audibly communicating questions and responses from the interviewer through the speaker of the computer system to the interviewee in the interviewee's language.

20. An interactive electronic communications process in accordance with claim 17 including:

transporting, supporting and operating the computer system in a translation station selected from the group consisting of a portable carrying case, a mobile case, a briefcase, an case with input slots for ingress and egress of one or more retractable imputing devices, a hinged case having a base and a pivotable lid providing a top, a case with a paper output slot, a case with a paper tray slot, a case with extendable and retractable legs, a case with a collapsible struts, a case with a handle, briefcase, suitcase, a wheeled stand, a mobile kiosk tray, a slidable tray, a cart, a moveable support surface, and combinations of any of the preceding;

electronically identifying the person comprising the interviewee on the CPU;

said identifying comprising electronically inputting personal information about the interviewee from an electronic device into the CPU;

said personal information being selected from the group consisting of visual information, visual surveillance, blood type, fingerprint, biological information, non-invasive data, voice, speech, DNA information, face, eyes, race, nationality, name, birthdate, address, social security number, passport number, personal identification number (PIN), passport information, driver's license, identification card information, bar code, code, mug shot, electronic information strip, hologram, photograph, personal encrypted card information, scrambled personal information, pixilated information, skin texture, nose, jaws, eyes, teeth, dental information, facial information, computerized personal information, embedded personal information, algorithm based personal information, software supported personal information, and combinations thereof;

said electronic device being selected from the group consisting of a camera, web cam, electronic eye, electronic lens, video camera, cam corder, face scanner, three dimensional (3D) face scanner, voice recognition device, optical reader, eye scanner, iris scanner, cornea scanner, retina scanner, blood analyzer, DNA analyzer, scanner, identification card scanner, touch screen, touch pad, screen pad, keypad, keys, and electronic mouse;

the interviewee is selected from the group consisting of a man, woman, child, customer, patient, traveler, refugee, immigrant, suspected terrorist, suspected criminal, and victim;

electronically authenticating and verifying the electronic identity of the person in the CPU by electronically comparing the electronically inputted information in the CPU with electronic information about the person previously imputed and electronically stored in the CPU or downloaded into the CPU from a data base;

detecting biometric conditions of the person;

the biometric conditions being selected from the group consisting of behavior patterns, temperature changes, pulse readings, eye scan, cornea scan, iris scan, retina scan, facial expressions, mouth expressions, palm reading, nostril observations, finger print analysis, teeth identification, breathing patterns, gait, rhythm, speech, voice, sweating latency in typing, hesitation in providing information which should be known to the interviewee and combinations of any of the proceeding;

electronically feeding, inputting or transmitting the biometric conditions of the person into the CPU;

electronically comparing in the CPU the biometric conditions of the person with standardized biometric conditions from a data base;

generating an impulse if the biometric conditions of the person substantially differ from the standardized biometric conditions;

said impulse being selected from the group consisting of a warning signal, verbal signal, visual signal, false reading, stop action, electronic impulse, and combinations thereof; and transmitting electronic interactive communications from the CPU to the interviewee in a place selected from the group consisting of a hospital, doctor's office, trauma center, medical facility, remote area, military zone, occupied territory, terrorist area, enemy zone, border, government agency, passport control, prison, penitentiary, internment facility, police station, interview room, interrogation room, airport, railway station, shipping port, cruise ship, bus terminal, public concourse, library, museum, financial institution, bank, savings and loan facility, automatic teller machine (ATM), welfare agency, government agency, currency exchange, broker, credit card company, credit union, and debit card company.

* * * * *